United States Patent
Yamamura et al.

(10) Patent No.: US 9,408,382 B2
(45) Date of Patent: Aug. 9, 2016

(54) METHOD FOR PRODUCING AGRICHEMICAL-CONTAINING RESIN COMPOSITION

(75) Inventors: Satoru Yamamura, Takaoka (JP); Yuichi Maekawa, Fujieda (JP); Masayuki Sukekawa, Naka-gun (JP)

(73) Assignee: Nippon Soda Co., Ltd., Tokyo (JP)

( * ) Notice: Subject to any disclaimer, the term of this patent is extended or adjusted under 35 U.S.C. 154(b) by 287 days.

(21) Appl. No.: 13/131,963

(22) PCT Filed: Dec. 10, 2009

(86) PCT No.: PCT/JP2009/006759
§ 371 (c)(1),
(2), (4) Date: May 31, 2011

(87) PCT Pub. No.: WO2010/067609
PCT Pub. Date: Jun. 17, 2010

(65) Prior Publication Data
US 2011/0236452 A1    Sep. 29, 2011

(30) Foreign Application Priority Data
Dec. 12, 2008  (JP) ................................ 2008-317194

(51) Int. Cl.
| | | |
|---|---|---|
| A01N 25/10 | (2006.01) | |
| A01N 43/08 | (2006.01) | |
| A01N 43/40 | (2006.01) | |
| A01N 43/78 | (2006.01) | |
| A01N 43/88 | (2006.01) | |
| A01N 47/40 | (2006.01) | |
| A01N 51/00 | (2006.01) | |

(52) U.S. Cl.
CPC ............... *A01N 25/10* (2013.01); *A01N 43/08* (2013.01); *A01N 43/40* (2013.01); *A01N 43/78* (2013.01); *A01N 43/88* (2013.01); *A01N 47/40* (2013.01); *A01N 51/00* (2013.01)

(58) Field of Classification Search
CPC ....... A01N 25/10; A01N 43/40; A01N 47/40; A01N 51/00; A01N 43/78; A01N 43/08; A01N 43/88
USPC .......... 424/405, 409, 489, 501; 514/341, 357, 514/229.2, 342, 365, 471
See application file for complete search history.

(56) References Cited

U.S. PATENT DOCUMENTS

| | | | |
|---|---|---|---|
| 2,897,121 A | 7/1959 | Wagner et al. | |
| 2007/0224233 A1* | 9/2007 | Maekawa et al. | 424/409 |
| 2009/0093364 A1* | 4/2009 | Endo et al. | 504/100 |

FOREIGN PATENT DOCUMENTS

| | | |
|---|---|---|
| CN | 1330695 | 1/2002 |
| CN | 1358433 | 7/2002 |
| CN | 1993044 | 7/2007 |
| EP | 1982590 | 10/2008 |
| EP | 2305029 A1 | 4/2011 |
| JP | 08-092007 | 4/1996 |
| JP | 11-269016 | 10/1999 |
| JP | 11-315004 | 11/1999 |
| JP | 2010/004730 A1 | 1/2010 |
| WO | 99/51091 | 10/1999 |
| WO | 2006/013972 | 2/2006 |
| WO | 2007/091494 | 8/2007 |

OTHER PUBLICATIONS

International Search Report issued for PCT/JP2009/006759, mailed on Feb. 2, 2010, 4 pages.
Office Action issued in corresponding CN Patent Application No. 200980149273.X dated Mar. 7, 2013 with English translation, 17 pages.
EP Communication with a Supplementary European Search Report issued in EP Appln. No. 09831715.9, dated Mar. 3, 2014, 7 pages.
"Multiple Regression With Two Predictor Variables", XP002720082, Aug. 13, 2007, pp. 423-464, retrieved from the Internet: URL: http://www.sagepub.com/upm-data/16828_Chapter_11.pdf [retrieved on Feb. 11, 2014].

* cited by examiner

*Primary Examiner* — John Pak
*Assistant Examiner* — Nathan W Schlientz
(74) *Attorney, Agent, or Firm* — Kenyon & Kenyon LLP

(57) ABSTRACT

Disclosed is a method which can readily design an agricultural chemical-containing resin composition having a desired release rate history and can produce the agricultural chemical-containing resin composition. Specifically disclosed is a method for producing an agricultural chemical-containing resin composition, including: respectively selecting an acetamiprid content $Ac_{SA}$ and a hydrophilic white carbon content $Ca_{SA}$ in the composition relative to the total mass of acetamiprid, a styrene-maleic anhydride copolymer or a styrene-maleic anhydride copolymer-mixed resin, and hydrophilic white carbon, so as to satisfy the inequations of: $0.524 \times Ac_{SA} + 1.422 \times Ca_{SA} - 6.009 \leq 40\%$ by mass, $5\%$ by mass $\leq Ac_{SA} \leq 35\%$ by mass, and $Ca_{SA} \geq 0.1\%$ by mass; and mixing the acetamiprid, the styrene-maleic anhydride copolymer or the styrene-maleic anhydride copolymer-mixed resin, and the hydrophilic white carbon, so that the thus selected contents $Ac_{SA}$ and $Ca_{SA}$ can be achieved.

9 Claims, No Drawings

METHOD FOR PRODUCING AGRICHEMICAL-CONTAINING RESIN COMPOSITION

TECHNICAL FIELD

The present invention relates to a method for producing an agricultural chemical-containing resin composition from which the release of the agricultural chemical active ingredient is controlled.

Priority is claimed on Japanese Patent Application No. 2008-317194, filed Dec. 12, 2008, the content of which is incorporated herein by reference.

BACKGROUND ART

Agricultural chemical formulations in a solid state which contain agricultural chemical active ingredients are used as a spray into water such as in rice paddy fields. If an agricultural chemical active ingredient exhibits high water solubility, the agricultural chemical active ingredient may be released too quickly from the agricultural chemical formulation. If the release speed of the agricultural chemical active ingredient is too high, problems may arise in that phytotoxicity may occur, and a sufficient residual effect may become unobtainable.

In order to solve these problems, so far, agricultural chemical formulations from which the release of the agricultural chemical active ingredient is controlled, have been proposed and developed. For example, Patent Document 1 proposes an agricultural chemical-containing resin composition obtained by mixing: (a) at least one type of readily water-soluble agricultural chemical raw material; (b) a water-insoluble substance or a poorly water-soluble substance having a melting point or a softening point of 50° C. or higher but lower than 130° C.; and (c) white carbon, under heating at the melting point or the softening point of the substance (b) or a higher temperature but below 130° C.

Moreover, Patent Document 2 proposes: a release-controlled agricultural chemical formulation for water surface application having an excellent property to float and disperse, which comprises an agricultural chemical-containing resin composition comprising an agricultural chemical active ingredient, polyethylene, and hydrophobic silica; a production method thereof; and a release-controlled agricultural chemical composition.

However, even with such an agricultural chemical composition or an agricultural chemical formulation as described in Patent Documents 1 and 2, the control of the release of the agricultural chemical active ingredient is not always sufficient. Thus, there has been a demand for the development of agricultural chemical compositions from which the release of the agricultural chemical active ingredient is sufficiently controlled.

In addition, Patent Document 3 proposes an agricultural chemical formulation wherein a composition comprising an agricultural chemical active ingredient, a styrene-maleic anhydride copolymer, and a release-controlling agent (a water soluble polymer, silicon oxide, or a surfactant), is in a compatible state or forms a matrix. Furthermore, Patent Document 4 proposes an agricultural chemical formulation wherein a composition comprising an agricultural chemical active ingredient, a styrene-maleic anhydride copolymer, and a metal salt of a fatty acid as a release-controlling agent, is in a compatible state or forms a matrix. In Patent Documents 3 and 4, a composition using 50% by mass of hydrophilic white carbon is described as a comparative example. The composition exhibits a high initial burst (the release rate after 15 minutes from the addition to water), and after 72 hours falls to a state, being so-called dead stock, in which the release rate stops increasing.

Patent Documents

Patent Document 1: Japanese Unexamined Patent Application, First Publication No. H8-92007
Patent Document 2: Japanese Unexamined Patent Application, First Publication No. H11-315004
Patent Document 3: WO2006/013972
Patent Document 4: WO2007/091494

DISCLOSURE OF THE INVENTION

Incidentally, even with such a composition comprising an agricultural chemical active ingredient, a styrene-maleic anhydride copolymer, and a release-controlling agent, as described in Patent Document 3 above, it is necessary to carry out trials on various composition ratios of the agricultural chemical active ingredient, the styrene-maleic anhydride copolymer, and the release-controlling agent, so as to adjust the composition ratio to be optimum, so that an adequate level of initial burst can be exhibited, and also so that the release rate can keep increasing even after 72 hours. For this reason, a long time has been required to design an agricultural chemical-containing resin composition having a desired release rate history.

Accordingly, it is an object of the present invention to provide a method which can readily design an agricultural chemical-containing resin composition having a desired release rate history and can produce such an agricultural chemical-containing resin composition.

Therefore, the inventors of the present invention have conducted intensive studies with consideration of such situations of prior art. As a result, they found out that an agricultural chemical-containing resin composition having a desired release rate history can be readily produced by: preparing a plurality of compositions in different composition ratios; respectively obtaining the release rate histories thereof; analyzing the data of the release rates and the composition ratios by a linear least-squares method; deriving an equation to estimate a release rate from a composition ratio; and designing the composition ratio according to this estimation equation.

Moreover, they also found out that, it is possible, by selecting the composition ratio according to the method of the present invention, to readily design and produce a composition such that an adequate level of initial burst can be exhibited, and also such that the release rate can keep increasing even after 72 hours, even if the composition uses a hydrophilic white carbon that had been deemed to have an inappropriate release rate history as described in the comparative examples in Patent Documents 3 and 4, and like documents. The present invention was completed on the basis of these findings.

In other words, the present invention includes the following aspects.

[1] A method for producing an agricultural chemical-containing resin composition, including:

mixing an agricultural chemical active ingredient A having a water solubility of 100 ppm or higher at 25° C., a styrene-maleic anhydride copolymer or a styrene-maleic anhydride copolymer-mixed resin, and a white carbon, at arbitrary composition ratios, so as to prepare a plurality of types of compositions;

respectively granulating these compositions to have an average particle diameter from 10 to 25 adding these granulated compositions to 25° C. distilled water, and measuring the release rate Y(t) (% by mass) of the agricultural chemical active ingredient A after t hours from the addition;

analyzing the content Ac (% by mass) of the agricultural chemical active ingredient A and the content Ca (% by mass) of the white carbon relative to the total mass of the agricultural chemical active ingredient A, the styrene-maleic anhydride copolymer or the styrene-maleic anhydride copolymer-mixed resin, and the white carbon, and the thus measured release rate Y(t), by a linear least-squares method, so as to obtain $$Y_{ev}(t) = a(t) \times Ac_S + b(t) \times Ca_S + c(t) \quad \text{Equation (I)}$$

(provided that, in the Equation (I): the symbol $Y_{ev}(t)$ represents the estimated release rate (% by mass) of the agricultural chemical active ingredient A after t hours from the addition; the symbols $a(t)$, $b(t)$, and $c(t)$ represent coefficients after t hours obtained from the linear least-squares method; the parameter t represents the elapsed time (hr) after the addition; the symbols $Ac_S$ and $Ca_S$ respectively represent the content (% by mass) of the agricultural chemical active ingredient A and the content (% by mass) of the white carbon relative to the total mass of the agricultural chemical active ingredient A, the styrene-maleic anhydride copolymer or the styrene-maleic anhydride copolymer-mixed resin, and the white carbon);

selecting a content $Ac_S$ of the agricultural chemical active ingredient A from a range not lower than 5% by mass and not higher than 35% by mass, and a content $Ca_S$ of the white carbon from a range not lower than 0.1% by mass, so that the estimated release rate $Y_{ev}(0.25)$ of the agricultural chemical active ingredient A after 15 minutes from the addition to 25° C. distilled water be not higher than 40% by mass in the Equation (I); and mixing the agricultural chemical active ingredient A, the styrene-maleic anhydride copolymer or the styrene-maleic anhydride copolymer-mixed resin, and the white carbon, so that the thus selected contents $Ac_S$ and $Ca_S$ can be achieved.

[2] The method for producing an agricultural chemical-containing resin composition according to [1], wherein the agricultural chemical active ingredient A is a neonicotinoid-based compound.

[3] The method for producing an agricultural chemical-containing resin composition according to [1], wherein the agricultural chemical active ingredient A is at least one type of compound selected from the group consisting of nitenpyram, imidacloprid, acetamiprid, thiamethoxam, clothianidin, thiacloprid, and dinotefuran.

[4] A method for producing an agricultural chemical-containing resin composition, including:

respectively selecting an acetamiprid content $Ac_{SA}$ and a hydrophilic white carbon content $Ca_{SA}$ relative to the total mass of acetamiprid, a styrene-maleic anhydride copolymer or a styrene-maleic anhydride copolymer-mixed resin, and hydrophilic white carbon, from a range satisfying the inequations of: $0.524 \times Ac_{SA} + 1.422 \times Ca_{SA} - 6.009 \leq 40\%$ by mass, $5\%$ by mass $\leq Ac_{SA} \leq 35\%$ by mass, and $Ca_{SA} \geq 0.1\%$ by mass; and mixing the acetamiprid, the styrene-maleic anhydride copolymer or the styrene-maleic anhydride copolymer-mixed resin, and the hydrophilic white carbon, so that the thus selected contents $Ac_{SA}$ and $Ca_{SA}$ can be achieved.

[5] The method for producing an agricultural chemical-containing resin composition according to any one of [1] to [4], wherein the hydrophobicity of the white carbon is 20% or lower.

[6] The method for producing an agricultural chemical-containing resin composition according to any one of [1] to [5], wherein the styrene-maleic anhydride copolymer-mixed resin is a mixture of a styrene-maleic anhydride copolymer with rosin or a derivative thereof, or, alternatively, a polymer having a repeating unit derived from salicylic acid or a derivative thereof.

[7] An agricultural chemical-containing resin composition produced by the production method according to any one of [1] to [6].

[8] An agricultural chemical-containing resin composition comprising acetamiprid, a styrene-maleic anhydride copolymer or a styrene-maleic anhydride copolymer-mixed resin, and hydrophilic white carbon, wherein the acetamiprid content $Ac_{SA}$ and the hydrophilic white carbon content $Ca_{SA}$ relative to the total mass of the acetamiprid, the styrene-maleic anhydride copolymer or the styrene-maleic anhydride copolymer-mixed resin, and the hydrophilic white carbon satisfy the inequations of: $0.524 \times Ac_{SA} + 1.422 \times Ca_{SA} - 6.009 \leq 40\%$ by mass, $5\%$ by mass $\leq Ac_{SA} \leq 35\%$ by mass, and $Ca_{SA} \geq 0.1\%$ by mass.

[9] A bulk powder comprising the agricultural chemical-containing resin composition according to [7] or [8].

[10] An agricultural chemical formulation including the bulk powder according to [9].

[11] The agricultural chemical formulation according to [10], wherein the average particle diameter of the bulk powder is 200 μm or smaller.

[12] A method for producing an agricultural chemical formulation, including granulating the agricultural chemical-containing resin composition according to [7] or [8].

[13] The method for producing an agricultural chemical formulation according to [12], wherein the granulation is performed by at least one type of method selected from the group consisting of a tumbling granulation process, an agitation granulation process, an extrusion granulation process, a rolling granulation process, a crushing granulation process, and a fluidized granulation process.

EFFECT OF THE INVENTION

The method for producing an agricultural chemical-containing resin composition of the present invention is capable of readily designing and producing an agricultural chemical-containing resin composition and an agricultural chemical formulation with which the phenomenon, namely initial burst, in which the agricultural chemical active ingredient is abundantly released within a short period of time, is suppressed to an adequate level, and the phenomenon, namely dead stock, in which the agricultural chemical active ingredient that should be fundamentally released but nonetheless remains by failing to be completely released, is suppressed. In addition, with the agricultural chemical-containing resin composition and the agricultural chemical formulation of the present invention, phytotoxicity due to the increase of the crop residue amount of the agricultural chemical active ingredient would not occur while maintaining the residual effect, and furthermore, remaining in the environment can be avoided. Moreover, in addition to the above-mentioned effects, the agricultural chemical-containing resin composition and the agricultural chemical formulation of the present invention have an effect to improve the residual effect of the agricultural chemical active ingredient, an effect to reduce the wash out into the environment, an effect to reduce the total spay amount, an effect to reduce the number of times of spraying, and an effect to alleviate the toxicity to the sprayer, because of the enhanced light stability, the volatility control, and the enhanced rain resistance, and thus are particularly useful as a seed treating agent and a soil treating agent.

BEST MODE FOR CARRYING OUT THE INVENTION

Agricultural Chemical-containing Resin Composition

The method for producing an agricultural chemical-containing resin composition of the present invention includes:

mixing an agricultural chemical active ingredient A having a water solubility of 100 ppm or higher at 25° C., a styrene-maleic anhydride copolymer or a styrene-maleic anhydride copolymer-mixed resin, and a white carbon, at arbitrary composition ratios, so as to prepare a plurality of types of compositions:

respectively granulating these compositions to have an average particle diameter from 10 to 25 μm, adding these granulated compositions to 25° C. distilled water, and measuring the release rate Y(t) (% by mass) of the agricultural chemical active ingredient A after t hours from the addition;

analyzing the content Ac (% by mass) of the agricultural chemical active ingredient A and the content Ca (% by mass) of the white carbon relative to the total mass of the agricultural chemical active ingredient A, the styrene-maleic anhydride copolymer or the styrene-maleic anhydride copolymer-mixed resin, and the white carbon, and the thus measured release rate Y(t), by a linear least-squares method, so as to obtain $$Y_{ev}(t) = a(t) \times Ac_S + b(t) \times Ca_S + c(t) \qquad \text{Equation (I)}$$

(provided that, in the Equation (I): the symbol $Y_{ev}(t)$ represents the estimated release rate (% by mass) of the agricultural chemical active ingredient A after t hours from the addition; the symbols a(t), b(t), and c(t) represent coefficients after t hours obtained from the linear least-squares method; the parameter t represents the elapsed time (hr) after the addition; the symbols $Ac_S$ and $Ca_S$ respectively represent the content (% by mass) of the agricultural chemical active ingredient A and the content (% by mass) of the white carbon relative to the total mass of the agricultural chemical active ingredient A, the styrene-maleic anhydride copolymer or the styrene-maleic anhydride copolymer-mixed resin, and the white carbon);

selecting a content $Ac_S$ of the agricultural chemical active ingredient A from a range not lower than 5% by mass and not higher than 35% by mass, and a content $Ca_S$ of the white carbon from a range not lower than 0.1% by mass, so that the estimated release rate $Y_{ev}(0.25)$ of the agricultural chemical active ingredient A after 15 minutes from the addition to 25° C. distilled water be not higher than 40% by mass in the Equation (I); and mixing the agricultural chemical active ingredient A, the styrene-maleic anhydride copolymer or the styrene-maleic anhydride copolymer-mixed resin, and the white carbon, so that the thus selected contents $Ac_S$ and $Ca_S$ can be achieved.

(Agricultural Chemical Active Ingredient A)

The agricultural chemical active ingredient A for use in the present invention has a water solubility of 100 ppm or higher, and preferably 500 ppm or higher, at 25° C. Regarding the agricultural chemical active ingredient A, it is possible to use compounds that are generally used as agricultural chemicals, such as a bactericide, an insecticide, an acaricide, a plant growth regulator, a herbicide, a rodenticide, an antibacterial agent, an antifungal agent, and an antialgae agent. These compounds can be used alone or as a mixture of two or more types.

The agricultural chemical active ingredient A can be exemplified by neonicotinoid-based compounds such as nitenpyram (water solubility: 590000 ppm (20° C.)), acetamiprid (water solubility: 4250 ppm (25° C.)), imidacloprid (water solubility: 510 ppm (20° C.)), thiamethoxam (water solubility: 4100 ppm (20° C.)), clothianidin (water solubility: 327 ppm (20° C.)), thiacloprid (water solubility: 185 ppm (20° C.)), and dinotefuran (water solubility: 54300 ppm (20° C.)); phosphorus-based compounds such as acephate (water solubility: 790000 ppm (20° C.)), N'-(4-chloro-o-toluoyl)-N,N-dimethylformamide (water solubility: 250 ppm (20° C.)), and DDVP (water solubility: about 18000 ppm (25° C.)); carbamate-based compounds such as bendiocarb (water solubility: 280 ppm (20° C.)), cartap (water solubility: 200000 ppm (20° C.)), and ethiofencarb (water solubility: 1800 ppm (20° C.)); and other insecticidal compounds such as oxamyl (water solubility: 280000 ppm (25° C.)), methomyl (water solubility: 58000 ppm (20° C.)), and D-D (water solubility: 2000 ppm (20° C.)). Of these, preferred are neonicotinoid-based compounds, more preferred are nitenpyram, acetamiprid, imidacloprid, thiamethoxam, clothianidin, thiacloprid, and dinotefuran, and particularly preferred is acetamiprid.

(Styrene-maleic Anhydride Copolymer or Styrene-maleic Anhydride Copolymer-mixed Resin)

The term "styrene-maleic anhydride copolymer" used in the present invention includes resins made by copolymerization reactions between styrene and maleic anhydride, and derivatives thereof. These derivatives can be exemplified by resins made by copolymerization reactions between styrene and maleic anhydride and then esterified by an alcohol, sulfonated by a sulfonating agent, or imidized by an amine, and neutralized products of the above esterified resins. Regarding these derivatives, preferred are resins esterified by an alcohol. The form of the polymerization of the styrene-maleic anhydride copolymer is not particularly limited. The monomer units may be randomly repeated or may be repeated in a block shape. Also, the form of the molecular chain may be either straight or branched. Such a branched molecular chain can be made by, for example, graft polymerization.

The term "styrene-maleic anhydride copolymer-mixed resin" refers to a mixture of a styrene-maleic anhydride copolymer as mentioned above and a different type of resin. The different type of resin for supplying to the mixture can be exemplified by a polyolefin-based resin, a poly(meth)acrylate-based resin, a polystyrene-based resin, a polyester-based resin, a polyvinyl chloride-based resin, a polyvinylidene chloride resin, a polyamide resin, a polyacetal resin, a polycarbonate resin, and a polyurethane resin.

Examples of the polyolefin-based resin include: polyethylene resins such as low density polyethylene, medium density polyethylene, high density polyethylene, polyethylene wax, and ethylene-α-olein copolymer elastomers; ethylene/vinyl acetate copolymers, ethylene/(meth)acrylic acid copolymers, polypropylene, propylene/ethylene copolymers, ethylene/propylene copolymers, polybutene, ethylene/propylene/butadiene copolymers; and the like.

Examples of the poly(meth)acrylate-based resins include: methyl methacrylate homopolymers; (meth)acrylate-based copolymers made by copolymerizing either an acrylic acid alkyl ester or a methacrylic acid allyl ester with a different type of monomer such as ethylene, styrene, α-methylstyrene, and acrylonitrile; impact resistant (meth)acrylic resins made by copolymerizing a (meth)acrylic acid alkyl ester, butadiene, styrene, and acrylonitrile; and the like.

Examples of the polystyrene-based resins include: styrene homopolymers; high impact polystyrene (HIPS), methyl methacrylate/butadiene/styrene copolymers, styrene/(meth) acrylic acid copolymers, and styrene/acrylonitrile copolymers; and the like.

Examples of the polyester-based resins include: aromatic polyesters such as polyethylene terephthalate, polybutylene terephthalate, polyethylene naphthalate; polyesters made by condensation of diols and dicarboxylic acid, which are used for resins for coating and such applications; and the like. Of these, preferred is an aliphatic polyester made by condensation polymerization of an aliphatic diol and a dicarboxylic acid.

In addition, examples of the polyester-based resins also include polyhydroxyalkanoate copolymers typified by 3-hydroxybutyrate/3-hydroxyvalerate copolymers, homopolymers composed solely of hydroxyalkanoate typified by polylactic acid, polycaprolactone, and copolymers of polylactic acid and polyester, and such biodegradable resins.

Examples of the polyvinyl chloride-based resins include: vinyl chloride homopolymers; copolymers of vinyl chloride with a different type of monomer such as ethylene, propylene, acrylonitrile, vinylidene chloride, vinyl acetate; and the like.

Of these resins, preferred is rosin or a derivative thereof, or, alternatively, a polymer having a repeating unit derived from salicylic acid or a derivative thereof, in terms of the compatibility with the agricultural chemical active ingredient and the property to control the release of the agricultural chemical active ingredient.

Rosin is a natural resin yielded from pine plants. The main components are abietic acid, isomers thereof, and the like. It is known that carboxyl groups of abietic acid are highly reactive, and thus are capable of producing various rosin derivatives by reacting with compounds having functional groups such as an epoxy group, a silanol group, an alkoxysilane group, a hydroxyl group, an amino group, an imino group, an isocyanate group, a blocked isocyanate group, a cyclocarbonate group, a vinyl ether group, a vinyl thioether group, an aminomethylol group, an alkylated aminomethylol group, an acetal group, and a ketal group. Specific examples of such rosin derivatives include tall rosin, rosin-modified phenol, and rosin-modified maleic acid.

Examples of the polymer having a repeating unit derived from salicylic acid or a derivative thereof include: polymers made by condensation of salicylic acid or a derivative thereof; polymers made by condensation of salicylic acid or a derivative thereof with a different type of hydroxycarboxylic acid; and the like. Commercially available polymers having a repeating unit derived from salicylic acid or a derivative thereof can be exemplified by linear polysalicylate manufactured by PROVIRON and the like.

The styrene-maleic anhydride copolymer-mixed resin is not specifically limited in terms of the blend ratio of a styrene-maleic anhydride copolymer to a different type of resin. For example, if rosin or a derivative thereof, or, alternatively, a polymer having a repeating unit derived from salicylic acid or a derivative thereof, is used as the different type of resin, the blend ratio of the styrene-maleic anhydride copolymer is preferably from 30 to 99% by mass, and more preferably from 50 to 99% by mass, relative to the weight of the mixed resin.

(White Carbon)

The term "white carbon" used in the present invention refers to those called synthetic amorphous silica, hydrated silicate, wet silica, or synthetic silicate. The average diameter of primary particles of the white carbon is preferably from 0.5 to 100 nm. Moreover, although white carbon usually has a Si—O network structure, in the present invention it is preferable to use a type of white carbon which has no fixed crystal structure (that is, amorphous silicon dioxide powder). It is preferable that the white carbon is hydrophilic. Specifically speaking, the hydrophobicity of the white carbon is preferably 20% or lower, more preferably 5% or lower, and particularly preferably 0%.

The hydrophobicity was measured by the following procedure. First, 0.2 g of white carbon was weighed and put in a 200 ml beaker. Then, 50 ml of distilled water was added thereto, and the mixture was stirred with a magnetic stirrer. While stirring the solution, methanol was gradually added therein dropwise by using a pipette. The point at which floating powder on the surface of the solution can not be observed, was deemed as the end point. Then, the hydrophobicity was calculated from the following equation.

$$\text{Hydrophobicity (\%)} = x/(50+x) \times 100$$

Note that, the symbol x represents the amount of methanol added therein (ml).

Commercially available hydrophilic white carbon can be exemplified by: "Carplex #80", "Carplex #67", "Carplex #1120", and "Carplex XR", which are product names manufactured by DSL. Japan Co., Ltd; "Nipsil NS-T", "Nipsil NS-K", and "Nipsil NA", which are product names manufactured by Tosoh Silica Corp.; "AEROSIL 200", which is a product name manufactured by Nippon Aerosil Co. Ltd.; and "Finesil" and "Tokusil", which are product names manufactured by Tokuyama Corp.

In the method for producing an agricultural chemical-containing resin composition of the present invention, firstly, the agricultural chemical active ingredient A, the styrene-maleic anhydride copolymer or the styrene-maleic anhydride copolymer-mixed resin (hereunder, may be referred to as "poorly water-soluble resin"), and the white carbon, as mentioned above, are mixed at arbitrary composition ratios so as to prepare a plurality of types of compositions.

Although the method for preparing these compositions is not specifically limited as long as the method is able to homogeneously mix the agricultural chemical active ingredient A, the poorly water-soluble resin, and the white carbon, in the present invention preferred are a melting method, a solvent method, and a pH precipitation method. In any preparation method, it is preferable to dissolve or disperse the agricultural chemical active ingredient A or acetamiprid in a matrix comprising the poorly water-soluble resin.

The melting method is a preparation method having the steps of: melting the agricultural chemical active ingredient A, the poorly water-soluble resin, and the white carbon under heating; and kneading the mixture.

More specifically, the melting method can be exemplified by: a method in which the poorly water-soluble resin is placed in a kneader or such a device and melted under heating, the agricultural chemical active ingredient A and the white carbon are respectively added thereto, and then the mixture is melted and kneaded; and a method in which the agricultural chemical active ingredient A, the poorly water-soluble resin, and the white carbon are mixed, and this mixture is melted under heating and kneaded in a continuous heating kneader or such a device.

The temperature for melting during the melting method is not specifically limited as long as the agricultural chemical active ingredient A is not decomposed but can be sufficiently compatibilized with or homogeneously mixed with the poorly water-soluble resin at this temperature. In the melting method, it is desirable to carry out the melting and kneading process at as low a temperature as possible so as to avoid decomposition of the agricultural chemical active ingredient A by heat, as well as doing it within a short period of time. However, when the temperature for melting is set too low, it may be sometimes difficult to achieve the sufficiently compatible state or the homogeneously mixed state because the viscosity of the melted product increases. Therefore, it is preferable to melt the mixture by adding a surfactant. By adding a surfactant, it may become possible to obtain a homogeneous composition even in a highly viscous state.

The solvent method is a preparation method having the steps of: dissolving or dispersing the agricultural chemical active ingredient A, the poorly water-soluble resin, and the white carbon, in an organic solvent to make the mixture homogeneous; and then removing the organic solvent by distillation.

More specifically, the solvent method can be exemplified by a method in which a solvent is charged in a container, then the poorly water-soluble resin and the agricultural chemical active ingredient A are respectively added thereto, the mixture is stirred under heating to completely dissolve the poorly water-soluble resin and the agricultural chemical active ingredient A in the solvent, the white carbon is added and dispersed therein, and thereafter the solvent is completely removed by distillation.

The solvent used in the solvent method is not particularly limited as long as the poorly water-soluble resin and the agricultural chemical active ingredient A to be used can be dissolved and stably present with the solvent. Examples thereof include: aromatic or aliphatic hydrocarbons such as xylene, toluene, alkyl naphthalene, phenylxylylethane, kerosene, gas oil, hexane, and cyclohexane; halogenated hydrocarbons such as chlorobenzene, dichloromethane, dichloroethane, and trichloroethane; alcohols such as methanol, ethanol, isopropyl alcohol, butanol, hexanol, and ethylene glycol; ethers such as diethyl ether, ethylene glycol dimethyl ether, tetrahydrofuran, and dioxane; esters such as ethyl acetate and butyl acetate; ketones such as acetone, methyl ethyl ketone, methyl isobutyl ketone, and cyclohexanone; nitriles such as acetonitrile and isobutyronitrile; acid amides such as dimethylsulfoxide, N,N-dimethylformamide, and N,N-dimethylacetamide; and vegetable oils such as soybean oil and cottonseed oil. Of these, particularly preferred are dichloromethane, acetone, and methanol.

The amount of the solvent used in the solvent method is not particularly limited as long as the agricultural chemical active ingredient A and the poorly water-soluble resin can be dissolved with the solvent of this amount. The amount is preferably within a range from 10 to 20% by mass relative to the total amount of the agricultural chemical active ingredient A and the poorly water-soluble resin.

It is desirable to carry out the production by dissolving the ingredients with as little amount of solvent as possible because costs will not be wasted on removing the solvent by distillation. However, when the amount of solvent is small, it may be sometimes difficult by stirring to obtain a resin in a compatible state or a homogeneously mixed state because the viscosity increases. Therefore, it is preferable to dissolve the ingredients with a solvent by adding a surfactant. By adding a surfactant, it may become possible to obtain a homogeneous composition even in a highly viscous state.

The temperature for dissolving the agricultural chemical active ingredient A and the poorly water-soluble resin with a solvent is preferably from 20 to 40° C. so as to keep the agricultural chemical active ingredient A stable.

A usual method can be employed as a method to remove the solvent by distillation. Specific examples thereof can include a reduced-pressure distillation method, a heat distillation method, and a reduced-pressure heat distillation method. In addition, a method using a spray drying granulator can also be used. Furthermore, it is also possible to exemplify a method in which a poor solvent is added to the agricultural chemical active ingredient A and the poorly water-soluble resin so as to precipitate the agricultural chemical active ingredient A and the poorly water-soluble resin, and then the precipitate is filtrated.

In the melting method and the solvent method, the order of sequence to melt or dissolve the agricultural chemical active ingredient A, the poorly water-soluble resin, and the white carbon is not specifically limited. It is possible to melt or dissolve them either at the same time or at different timings. Moreover, it is also possible to melt or dissolve predetermined amounts of the agricultural chemical active ingredient A, the poorly water-soluble resin, and the white carbon, at several separate timings. Furthermore, depending on the composition ratio, both the solvent method and the melting method can be applied together.

The pH precipitation method is a preparation method having the steps of: preparing an alkaline solution which contains the poorly water-soluble resin, the agricultural chemical active ingredient A, and the white carbon; and thereafter acidifying the pH of this solution.

More specifically, the pH precipitation method can be exemplified by a method in which the poorly water-soluble resin and the agricultural chemical active ingredient are added and completely dissolved in an ammonium solution, the white carbon is added and dispersed therein, then hydrochloric acid is added to acidify the pH of this solution so as to precipitate the ingredients, and this precipitate is filtrated and dried.

The thus prepared composition by the above-mentioned method is granulated to have an average particle diameter (from 10 to 25 μm) that is suitable for measuring the release rate. The granulation can be performed by at least one type of method selected from the group consisting of a tumbling granulation process, an agitation granulation process, an extrusion granulation process, a rolling granulation process, a crushing granulation process, and a fluidized granulation process. During the granulation of the composition, a granulation auxiliary agent such as a surfactant can be added.

In the present invention, granulation by means of a crushing granulation process is preferably employed so as to adjust the average particle diameter. In the crushing granulation process, it is possible to use a pulverizer for use in the production of extrusion-molded granules, or a pin mill, a jet mill, or such a mill for use in the production of wettable powders. Moreover, in cases where the agricultural chemical-containing resin composition is produced by the solvent method, it is possible, by using a spray drying granulator, to concurrently perform the removal of the solvent by distillation and the granulation.

The release rate was measured by the following manner. The granulated compositions were respectively weighed precisely so that each sample can contain 10 mg of the agricultural chemical active ingredient A, and put in a 100 ml vial container. Then, 80 ml of 25° C. distilled water and 20 ml of a methyl 4-hydroxybenzoate solution (500 mg/liter of distilled water) as an internal standard were added therein. The container was sealed, inverted five times, and left still in a thermostatic chamber at 25° C. until the time of sampling. After a predetermined period of time, the container was inverted five times. Next, about 0.7 ml of the solution was sampled out (filtrated with a 0.45 μm filter). The concentration of the agricultural chemical active ingredient A in the sampled solution was measured by HPLC. The release rate was calculated by percentage with respect to the concentration of the agricultural chemical active ingredient A assuming that the agricultural chemical active ingredient A in the composition had been all dissolved with water.

This measurement gives a plurality of data showing the relation between the content Ac (% by mass) of the agricultural chemical active ingredient A and the content Ca (% by mass) of the white carbon in the composition, relative to the total mass of the agricultural chemical active ingredient A, the poorly water-soluble resin, and the white carbon, and the measured release rate Y(t) after t hours from the addition.

These data were analyzed by a linear least-squares method, and $$Y_{ev}(t)=a(t) \times Ac_S + b(t) \times Ca_S + c(t) \qquad \text{Equation (I)}$$

(provided that, in the Equation (I): the symbol $Y_{ev}(t)$ represents the estimated release rate (% by mass) of the agricultural chemical active ingredient A after t hours from the addition; the symbols a(t), b(t), and c(t) represent coefficients after t hours obtained from the linear least-squares method; the parameter t represents the elapsed time (hr) after the addition; the symbols $Ac_S$ and $Ca_S$ respectively represent the content (% by mass) of the agricultural chemical active ingredient A and the content (% by mass) of the white carbon relative to the total mass of the agricultural chemical active ingredient A, the poorly water-soluble resin, and the white carbon) is obtained.

By the above-mentioned calculation method, the Equation (Ia) to obtain the estimated release rate $Y_{ev}(0.25)$ of the agricultural chemical active ingredient A after 15 minutes from the addition to 25° C. distilled water, and the Equation (IIa) to obtain the estimated release rate $Y_{ev}(120)$ of the agricultural chemical active ingredient A after 120 hours from the addition to 25° C. distilled water, can be given.

$$Y_{ev}(0.25)=a(0.25) \times Ac + b(0.25) \times Ca + c(0.25) \qquad \text{Equation (Ia)}$$

$$Y_{ev}(120)=a(120) \times Ac + b(120) \times Ca + c(120) \qquad \text{Equation (IIa)}$$

For example, when acetamiprid is used as the agricultural chemical active ingredient A and hydrophilic white carbon is used as the white carbon, the Equation 1a and the Equation 2a can be given by the above-mentioned calculation method.

$$Y_{evA}(0.25)=0.524 \times Ac_{SA} + 1.422 \times Ca_{SA} - 6.009 \qquad \text{Equation 1a}$$

$$Y_{evA}(120)=1.545 \times Ac_{SA} + 2.945 \times Ca_{SA} - 7.562 \qquad \text{Equation 2a}$$

In the Equation 1a and the Equation 2a, the symbol $Y_{evA}(0.25)$ represents the estimated release rate of acetamiprid after 15 minutes from the addition to 25° C. distilled water; the symbol $Y_{evA}(120)$ represents the estimated release rate of acetamiprid after 120 hours from the addition to 25° C. distilled water; the symbol $Ac_{SA}$ represents the acetamiprid content in the composition relative to the total mass of the acetamiprid, the poorly water-soluble resin, and the hydrophilic white carbon; and the symbol $Ca_{SA}$ represents the hydrophilic white carbon content in the composition relative to the total mass of the acetamiprid, the poorly water-soluble resin, and the hydrophilic white carbon.

Then, the content $Ac_S$ of the agricultural chemical active ingredient A in the composition relative to the total mass of the agricultural chemical active ingredient A, the poorly water-soluble resin, and the white carbon, is selected from a range not lower than 5% by mass and not higher than 35% by mass, and the content $Ca_S$ of the white carbon in the composition relative to the total mass of the agricultural chemical active ingredient A, the poorly water-soluble resin, and the white carbon, is selected from a range not lower than 0.1% by mass, so as to satisfy the inequation of: estimated release rate $Y_{ev}(0.25) \leq 40\%$ by mass, and preferably 6% by mass $\leq$ estimated release rate $Y_{ev}(0.25) \leq 20\%$ by mass.

For example, when acetamiprid is used as the agricultural chemical active ingredient A and hydrophilic white carbon is used as the white carbon, $Ac_{SA}$ and $Ca_{SA}$ are respectively selected from a range satisfying the inequations of: estimated release rate $Y_{evA}(0.25)=0.524 \times Ac_{SA} + 1.422 \times Ca_{SA} - 6.009 \leq 40\%$ by mass, 5% by mass $\leq Ac_{SA} \leq 35\%$ by mass, and $Ca_{SA} \geq 0.1\%$ by mass.

For example, when 30% by mass is selected as the acetamiprid content, the hydrophilic white carbon content is not lower than 0.1% by mass and not higher than 21.30% by mass.

Similarly, when 5% by mass is selected as the acetamiprid content, the hydrophilic white carbon content is not lower than 0.1% by mass and not higher than 30.51% by mass.

Similarly, when 35% by mass is selected as the acetamiprid content, the hydrophilic white carbon content is not lower than 0.1% by mass and not higher than 19.46% by mass.

Lastly, the agricultural chemical active ingredient A, the styrene-maleic anhydride copolymer or the styrene-maleic anhydride copolymer-mixed resin, and the white carbon are mixed so that the thus selected content $Ac_S$ of the agricultural chemical active ingredient A and the content $Ca_S$ of the white carbon can be achieved. By so doing, the target agricultural chemical-containing resin composition is prepared. The preparation method can be exemplified by the melting method, the solvent method, and the pH precipitation method as mentioned above. In order to enhance the precision to control the release rate, it is preferable to prepare the target agricultural chemical-containing resin composition by the same method as the preparation method that has been employed to prepare the compositions so as to obtain the estimated release rate.

The agricultural chemical-containing resin composition of the present invention obtained by the production method based on the estimated release rate $Y_{ev}(t)$ as mentioned above is preferably such that the content of the agricultural chemical active ingredient A be not lower than 5% by mass and not higher than 35% by mass and the content of the white carbon be not lower than 0.1% by mass, relative to the total mass of the agricultural chemical active ingredient A, the styrene-maleic anhydride copolymer or the styrene-maleic anhydride copolymer-mixed resin, and the white carbon, and the measured release rate Y(0.25) of the agricultural chemical active ingredient A after 15 minutes from the addition of the composition that has been granulated to have an average particle diameter from 10 to 25 μm to 25° C. distilled water be not higher than 40% by mass.

The agricultural chemical-containing resin composition of the present invention can be formed in appropriate sizes of particles so as to produce a bulk powder to be used for the agricultural chemical formulation. The average particle diameter of the bulk powder of the agricultural chemical-containing resin composition does vary depending on the purpose of application without any limitation. However, it is preferable to set the diameter to be 200 μm or smaller, and particularly preferably from 1 to 100 μm. In addition, regarding the bulk powder for use in the agricultural chemical formulation, it is possible to make a combination of two or more types of agricultural chemical-containing resin compositions of the present invention which have different grain sizes and constitutions. By making a combination in this way, the release speed of the agricultural chemical active ingredient A can be adjusted. Moreover, the bulk powder for use in the agricultural chemical formulation can also be prepared by separately using two or more types of agricultural chemical active ingredients A to produce types of agricultural chemical-containing resin compositions which are respectively suitable for respective types of ingredients, and then appropriately mixing these compositions.

Agricultural Chemical Formulation

The agricultural chemical formulation of the present invention comprises at least one type of agricultural chemical-containing resin composition of the present invention.

The agricultural chemical formulation of the present invention can use a formulation base material according to the purpose of application. Examples of the formulation base material include: release-controlling agents such as a water soluble polymer and a surfactant; inorganic salts such as calcium carbonate, potassium chloride, and sodium sulfate; organic acids such as citric acid, malic acid, fumaric acid, and stearic acid; and salts of such organic acids; sugars such as lactose and sucrose; inorganic additives such as alumina powder, silica gel, zeolite, hydroxyapatite, zirconium phosphate, titanium phosphate, silicon oxide, titanium oxide, zinc oxide, hydrotalcite, kaolinite, montmorillonite, talc, and clay; antioxidants such as n-propyl gallate and butylhydroxyanisole; pH adjusters and buffering agents such as sodium tripolyphosphate, sodium dihydrogen phosphate, and ammonium phosphate; colorants such as Food Blue No. 1, methylene blue, and pigment red 48; and other agents such as antiseptics, lubricants, ultraviolet absorbers, and antistatic agents.

Examples of the water soluble polymers include: natural water soluble polymers such as starch and gelatin; semisynthetic cellulose derivatives such as carboxymethyl cellulose, methyl cellulose, and hydroxypropyl cellulose; and synthetic water soluble polymers such as polyvinyl alcohol, polyacrylic acid based-polymers, polyacrylamide, and polyethylene glycol.

The surfactant is not limited as long as it can be used for usual agricultural chemical formulations. Specific examples of a nonionic surfactant include: sugar ester-type surfactants such as sorbitan fatty acid esters ($C_{12-18}$), POE sorbitan fatty acid esters ($C_{12-18}$), and sucrose fatty acid esters; fatty acid ester-type surfactants such as POE fatty acid esters ($C_{12-18}$), POE resin acid esters, and POE fatty acid diesters ($C_{12-18}$); alcohol-type surfactants such as POE alkyl ethers ($C_{12-18}$); alkyl phenol-type surfactants such as POE alkyl ($C_{8-12}$) phenyl ethers, POE dialkyl ($C_{8-12}$) phenyl ethers, and POE alkyl ($C_{8-12}$) phenyl ether formalin condensation products; polyoxyethylene/polyoxypropylene block polymer-type surfactants such as polyoxyethylene/polyoxypropylene block polymers and alkyl ($C_{12-18}$) polyoxyethylene/polyoxypropylene block polymer ethers; alkylamine-type surfactants such as POE allylamines ($C_{12-18}$) and POE fatty acid amides ($C_{12-18}$); bisphenol-type surfactants such as POE fatty acid bisphenol ethers; polyaromatic cyclic surfactants such as POA benzyl phenyl (or phenyl phenyl)ethers and POA styryl phenyl (or phenyl phenyl)ethers; silicon-based and fluorine-based surfactants such as POE ether-type silicon, POE ester-type silicon, and POE fluorine-based surfactants; and vegetable oil-type surfactants such as POE castor oil and POE hardened castor oil.

Examples of an anionic surfactant include: sulfate-type surfactants such as alkyl sulfates ($C_{12-18}$, Na, $NH_4$, and alkanolamine), POE alkyl ether sulfates ($C_{12-18}$, Na, $NH_4$, and alkanolamine), POE alkyl phenyl ether sulfates ($C_{12-18}$, $NH_4$, alkanolamine, and Ca), POE benzyl (or styryl) phenyl (or phenyl phenyl) ether sulfates (Na, $NH_4$, and alkanolamine), and polyoxyethylene/polyoxypropylene block polymer sulfates (Na, $NH_4$, and alkanolamine); sulfonate-type surfactants such as paraffin (alkane) sulfonates ($C_{12-22}$, Na, Ca, and alkanolamine), e), AOS ($C_{14-16}$, Na, and alkanolamine), dialkyl sulfosuccinates ($C_{8-12}$, Na, Ca, and Mg), alkyl benzene sulfonates ($C_{12}$, Na, Ca, Mg, $NH_4$, alkylamine, alkanol, amine, and cyclohexylamine), mono- or dialkyl ($C_{3-6}$) naphthalene sulfonates (Na, $NH_4$, alkanolamine, Ca, and Mg), naphthalene sulfonate/formalin condensation products (Na and $NH_4$), alkyl ($C_{8-12}$) diphenyl ether disulfonates (Na and $NH_4$), lignin sulfonates (Na and Ca), POE alkyl ($C_{8-12}$) phenyl ether sulfonates (Na), and POE alkyl ($C_{12-18}$) ether sulfosuccinic acid half esters (Na); POE alkyl ($C_{12-18}$) ether phosphates (Na and alkanolamine) such as carboxylic acid-type fatty acid salts ($C_{12-18}$, Na, K, $NH_4$, and alkanolamine), N-methyl-fatty acid sarcosinates ($C_{12-18}$ and Na), and resin acid salts (Na and K); and phosphate-type surfactants such as POE mono- or dialkyl ($C_{8-12}$) phenyl ether phosphates (Na and alkanolamine), POE benzylated (or styrylated) phenyl (or phenyl phenyl) ether phosphates (Na and alkanolamine), phosphatidylcholine/phosphatidylethanolimine (lecithin), and alkyl ($C_{8-12}$) phosphates.

Examples of a cationic surfactant include: ammonium-type surfactants such as alkyltrimethylammonium chlorides ($C_{12-18}$), methyl-polyoxyethylene-alkyl ammonium chlorides ($C_{12-18}$), allyl-N-methylpyridinium bromides ($C_{12-18}$), mono- or dialkyl ($C_{12-18}$) methylated ammonium chlorides, and alkyl ($C_{12-18}$) pentamethyl propylene diamine dichlorides; and benzalkonium-type surfactants such as alkyl dimethyl benzalkonium chlorides ($C_{12-18}$) and benzethonium chlorides (octyl phenoxy ethoxy ethyl dimethyl benzyl ammonium chlorides).

Examples of an amphoteric surfactant include: betaine-type surfactants such as dialkyl ($C_{8-12}$) diamino ethyl betaines and alkyl ($C_{12-18}$) dimethyl benzyl betaines; and glycine-type surfactants such as dialkyl ($C_{8-12}$) diamino ethyl glycines and alkyl ($C_{12-18}$) dimethyl benzyl glycines.

These surfactants can be used alone or as a mixture of two or more types.

The agricultural chemical formulation of the present invention may contain an agricultural chemical active ingredient B, in addition to the agricultural chemical active ingredient A contained in the agricultural chemical-containing resin composition of the present invention.

The agricultural chemical active ingredient B is not to be limited by whether it is liquid or solid, whether it is an organic compound or an inorganic compound, whether it consists of a single compound or a mixture of compounds, and the like. The agricultural chemical active ingredient B can be employed by selection from compounds generally used as agricultural chemicals, such as a bactericide, an insecticide, an acaricide, a plant growth regulator, a herbicide, a rodenticide, an antibacterial agent, an antifungal agent, and an anti-algae agent. These agricultural chemical active ingredients can be used alone or as a mixture of two or more types.

Examples of the bactericide as the agricultural chemical active ingredient B include: copper agents such as basic copper chloride and basic copper sulfate; sulfur agents such as thiuram, zineb, maneb, mancozeb, ziram, propineb, and polycarbamate; polyhaloalkylthio agents such as captan, folpet, and dichlorofluanid; organic chlorine agents such as chlorothalonil and fthalide; organic phosphorus agents such as IBP, EDDP, trichlophosmethyl, pyrazophos, and fosetyl; benzimidazole agents such as thiophanate-methyl, benomyl, carbendazim, and thiabendazole; dicarboxylmide agents such as iprodione, procymidone, vinclozolin, and fluoroimide; carboxyamide agents such as oxycarboxin, mepronil, flutolanil, tecloftalam, trichlamide, and pencycuron; acylalanine agents such as metalaxyl, oxadixyl, and furalaxyl; methoxyacrylate agents such as kresoxim-methyl, azoxystrobin, and metominostrobin; anilinopyrimidine agents such as andoprim, mepanipyrim, pyrimethanil, and diprozinil;

SBI agents such as triadimefon, triadimenol, bitertanol, myclobutanil, hexaconazole, propiconazole, triflumizole, prochloraz, pefurazoate, fenarimol, pyrifenox, triforine, flusilazole, etaconazole, dichlobutorazol, fluotrimazole, flutriafen, penconazole, diniconazole, imazalil, tridemorph, fenpropimorph, buthiobate, epoxiconazole, and metconazole; antibiotic agents such as polyoxins, blasticidin S, kasugamycin, validamycin, and dihydrostreptomycin sulfate; propamocarb hydrochloride, quintozene, hydroxyisoxazole, methasulfocarb, anilazine, isoprothiolane, probenazole, chinomethionat, dithianon, dinocap, diclomezine, ferimzone, fluazinam, pyroquilon, tricyclazole, oxolinic acid, dithianon, iminoctadine acetate, cymoxanil, pyrrolnitrin, methasulfocarb, diethofencarb, binapacryl, lecithin, sodium bicarbonate, fenaminosulf, dodine, dimethomorph, phenazine oxide, carpropamid, flusulfamide, fludioxonil, and famoxadon.

Examples of the insecticide/acaricide as the agricultural chemical active ingredient B include: organic phosphorus and carbamate-based insecticides such as fenthion, fenitrothion, diazinon, chlorpyrifos, ESP, vamidothion, phenthoate, dimethoate, formothion, malathion, trichlorfon, thiometon, phosmet, dichlorvos, acephate, EPBP, methyl parathion, oxydemeton-methyl, ethion, salithion, cyanophos, isoxathion, pyridafenthion, phosalone, methidathion, sulprofos, chlorfenvinphos, tetrachlorvinphos, dimethylvinphos, propaphos, isofenphos, ethylthiometon, profenofos, pyraclofos, monocrotophos, azinphos-methyl, aldicarb, methomyl, thiodicarb, carbofuran, carbosulfan, benfuracarb, furathiocarb, propoxur, BPMC, MTMC, MIPC, carbaryl, pirimicarb, ethiofencarb, and fenoxycarb;

pyrethroid-based insecticides such as permethrin, cypermethrin, deltamethrin, fenvalerate, fenpropathrin, pyrethrins, allethrin, tetramethrin, resmethrin, dimethrin, propathrin, phenothrin, prothrin, fluvalinate, cyfluthrin, cyhalothrin, flucythrinate, etofenprox, cycloprothrin, tralomethrin, silafluofen, brofenprox, and acrinathrin; benzoylurea-based and other insecticides such as diflubenzuron, chlorfluazuron, hexaflumuron, triflumuron, flufenoxuron, flucycloxuron, buprofezin, pyriproxyfen, methoprene, benzoepin, diafenthiuron, fipronil, cartap, thiocyclam, bensultap, nicotine sulfate, rotenone, metaldehyde, machine oil, BT or insect pathogenic viruses, and such microbial pesticides, and pheromone agents;

nematicides such as phenamiphos and fosthiazate; and acaricides such as chlorobenzilate, phenisobromolate, dicofol, amitraz, BPPS, benzomate, hexythiazox, fenbutatin oxide, polynactin, quinomethionate, CPCBS, tetradifon, avermectin, milbemectin, clofentezine, cyhexatin, pyridaben, fenpyroximate, tebufenpyrad, pyrimidifen, fenothiocarb, and dienochlor.

Examples of the plant growth regulator as the agricultural chemical active ingredient B include: gibberellins (for example, gibberellin A3, gibberellin A4, and gibberellin A7), IAA, and NAA.

Examples of the herbicide as the agricultural chemical active ingredient B include: anilide based herbicides such as diflufenican and propanil; chloroacetoanilide-based herbicides such as alachlor and pretilachlor; aryloxyallcanoic acid-based herbicides such as 2,4-D and 2-4-DB; aryloxyphenoxyalkanoic acid-based herbicides such as diclofop-methyl and fenoxaprop-ethyl; arylcarboxylic acid-based herbicides such as dicamba and pyrithiobac; imidazoline-based herbicides such as imazaquin and imazethapyr; urea-based herbicides such as diuron and isoproturon; carbamate-based herbicides such as chlorprofam and fenmedifam; thiocarbamate-based herbicides such as thiobencarb and EPTC; dinitroaniline-based herbicides such as trifluralin and pendimethalin; diphenyl ether-based herbicides such as acifluorfen and fomesafen; sulfonylurea-based herbicides such as bensulfuron-methyl and nicosulfuron; triazinone-based herbicides such as metribuzin and metamitron;

triazine-based herbicides such as atrazine and cyanazine; triazopyrimidine-based herbicides such as flumetsulam; nitrile-based herbicides such as bromoxinil and dichlobenil; phosphoric acid-based herbicides such as glyphosate and glufosinate; quaternary ammonium salt-based herbicides such as paraquat and difenzoquat; cyclic imide-based herbicides such as flumiclorac-pentyl and fluthiacet-methyl; benzoylaminopropionic acid-based herbicides such as benzoylprop-ethyl and furanprop-ethyl; isoxaben, ethofumesate, oxadiazon, piperophos, daimuron, bentazone, benfuresate, difenzo-quat, naproanilide, triazofenamide, quinclorac, clomazone, sulcotrione, cinmethylin, dithiopyr, pyrazolate, pyridate, flupoxam; and, in addition, cyclohexanedione-based herbicides such as sethoxydim and tralkoxydim.

Examples of the synergists/antidotes as the agricultural chemical active ingredient B include: octachlorodipropyl ether, piperonyl butoxide, cyneprin, IBTA, benoxacor, cloquintocet-methyl, cyometrinil, dichlormid, fenchlorazole-ethyl, fenclorim, flurazole, flaxofenimi, furilazole, mefenpyrdiethyl, MG191, naphthalic anhydride, oxabetrinil, and neonicotinoid-based compounds.

Examples of the antibacterial/antifungal/antialgae agent as the agricultural chemical active ingredient B include: trialkyltriamine, ethanol, isopropyl alcohol, propyl alcohol, trisnitro, chlorobutanol, bronopol, glutaraldehyde, formaldehyde, α-bromcinnamaldehyde, skane M-8, kathon CG, NS-500W, BIT, n-butyl BIT, allyl isothiocyanate, thiabendazole, methyl 2-benzimidazolyl carbamate, lauricidine, bioban, triclocarban, halocarban, glasisicar, benzoic acid, sorbic acid, caprylic acid, propionic acid, 10-undecylenic acid, potassium sorbate, potassium propionate, potassium benzoate, monomagnesium phthalate, zinc undecylenate, 8-hydroxyquinoline, copper quinoline, TMTD, triclosan, diclohelanilide, tolyfluanid, milt protein, egg white lysozyme, benthiazole, sodium carbam, triazine, tebuconazole, hinokitiol, tetrachloroisophthalonitrile, tectamer 38, chlorhexidine gluconate, chlorhexidine hydrochloride, polyhexamethylene biguanide, polybiguanide hydrochloride, dantobrom, clidant, sodium pyrithione, zinc pyrithione, densil, copper pyrithione, thymol, isopropyl methyl phenol, OPP, phenol, butyl paraben, ethyl paraben, methyl paraben, propyl paraben, metacresol, orthocresol, paracresol, sodium orthophenyl phenol, chlorophene, parachlorophenol, parachloromethaxylate, parachlorocresol, fluorfolpet, polylysine, bioban P-1487, Diiodomethylparatolylsulfone, polyvinylpyrrolidone parachloroisocyanel, hydrogen peroxide, stabilized chlorine dioxide, peracetic acid, copper naphthenate, novalon AG 300, silver chloride, titanium oxide, silver, zinc calcium phosphate, Silver Ace, silver zinc aluminosilicate, silver zinc zeolite, novalon AGZ330, phorone killer, dimer 136, benzalkonium chloride, didecyl dimethyl ammonium chloride, bardack 2250/80, benzethonium chloride, hyamine 3500J, cetylammonium bromide, cetrimide, CTAB, Cetavlon, Dimer-38, benzalkonium chloride, BARDAC 170P, DC-5700, cetyl pyridinium chloride, chitosan, diuron, DCMU, preventol A6, CMI, 2Cl-OIT, BCM, ZPT, BNP, OIT, IPBC, and TCMSP.

The agricultural chemical formulation of the present invention can be produced by using the agricultural chemical-containing resin composition of the present invention, and if needed, a formulation base material and an agricultural chemical active ingredient B as mentioned above, by a general production method for making a powder agent, a powder granule agent, a granule agent, a smoking agent, a pasting agent, a wettable powder, a granular wettable powder, a tablet, and a flowable formulation. Examples of such methods include methods in which the agricultural chemical-containing resin composition, and if needed, a formulation base material and an agricultural chemical active ingredient B as mentioned above, are mixed and then crushed/milled/granulated.

The agricultural chemical formulation of the present invention can be formed in various grain sizes according to the purpose of application. For example, in order to use the formulation as a formulation base material, a seed dressing, or a powder agent, it is preferable to set the diameter within a range of 200 μm or smaller, and particularly preferable a range from 1 to 100 μm. In addition, the release speed of the agricultural chemical active ingredient can be adjusted by making a combination of two or more types of agricultural chemical formulations of the present invention having different granule sizes and constitutions.

Moreover, it is also possible to use a plurality of types of agricultural chemical active ingredients to prepare several types of agricultural chemical formulations of the present invention per each ingredient, and then appropriately mix these formulations. By performing such a way of formulation by mixing, agricultural chemical active ingredients which are prone to be unstable when contacted to each other, or agricultural chemical active ingredients whose physical properties are remarkably different, can be combined into one formulation.

The agricultural chemical formulation of the present invention can be applied to both agricultural and non-agricultural areas, in the form of various types of treating agents. For example, it is possible to use the agricultural chemical formulation: as a seed treating agent to be applied to seed potatoes and the like by means of spraying treatment, dressing treatment, spray coating, immersion treatment, or the like; as a foliage treating agent to be applied by means of sprinkling treatment, top dressing treatment, or the like; as a soil treating agent to be applied by means of surface sprinkling treatment, soil incorporation treatment, soil drenching treatment, soil fumigation treatment, planting hole treatment, plant foot treatment, row treatment, seeding furrow treatment, seedling box treatment, seedling pot treatment, or the like; as a paddy treating agent to be applied by granule application, jumbo granule application, flowable application, or the like; and as other treating agents to be applied by means of fumigation treatment, lawn treatment, or the like. Of these, the agricultural chemical formulation of the present invention is preferably used as a seed treating agent or a soil treating agent.

EXAMPLES

Here is a more detailed description of the present invention with reference to Examples. However, the scope of the present invention is not to be limited to these Examples.
(Determination of Estimation Equation)

Pure acetamiprid, SMA17352P (a styrene-maleic anhydride copolymer having a molecular weight of 7000, manufactured by Sartomer Company Inc.), and Carplex #80D (hydrophilic white carbon having a hydrophobicity of 0%, manufactured by Shionogi & Co., Ltd.) were weighed out according to the formula shown in table 1, then dissolved and dispersed in about 200 ml of acetone. The solvent was removed by distillation using an evaporator, thereby yielding a solid matter. This solid matter was ground in a mortar. The ground matter was dried by a vacuum dryer at 40° C. for 2.5 hours, thereby yielding the compositions 1 to 9.

TABLE 1

|  | Pure acetamiprid (% by mass) | SMA17352P (% by mass) | Carplex #80D (% by mass) |
|---|---|---|---|
| Composition 1 | 5 | 94 | 1 |
| Composition 2 | 5 | 90 | 5 |
| Composition 3 | 5 | 85 | 10 |
| Composition 4 | 30 | 69 | 1 |
| Composition 5 | 30 | 65 | 5 |
| Composition 6 | 30 | 60 | 10 |
| Composition 7 | 35 | 64 | 1 |
| Composition 8 | 35 | 60 | 5 |
| Composition 9 | 35 | 55 | 10 |

44.1 g of the composition was added with 0.45 g of Newkalgen RX-B (sodium lignin sulfonate manufactured by Takemoto Oil & Fat Co., Ltd.) and 0.45 g of Newkalgen BX-C (sodium alkylnaphthalene sulfonate manufactured by Takemoto Oil & Fat Co., Ltd.), and well mixed. The mixture was pulverized using a pin mill to effect granulation into an average particle diameter within a range from 10 to 25 μm.

The resulting granulated matters were respectively weighed precisely so that each sample can contain 10 mg of pure acetamiprid, and put in a 100 ml vial container. Then, 80 ml of 25° C. distilled water and 20 ml of a methyl 4-hydroxybenzoate solution (500 mg/liter of distilled water) as an internal standard were added therein. The container was sealed, inverted five times, and left still in a thermostatic chamber at 25° C. until the time of sampling. After a predetermined period of time, the container was inverted five times. Next, about 0.7 ml of the solution was sampled out (filtrated with a 0.45 μm filter). The concentration of acetamiprid in the sampled solution was measured by HPLC. The release rate was calculated by percentage with respect to the concentration of acetamiprid assuming that acetamiprid in the composition had been all dissolved with water. The measurement was carried out for 120 hours.

Note that, the term "average particle diameter" used in Examples of the present invention means the volume average particle diameter resulting from the measurement with use of the MicroTrack 9320-X-100 manufactured by Nikkiso Co., Ltd.

On the basis of the above-measurement results, the Equation A to Equation E for estimating the release rate at respective time points were derived by a linear least-squares method, when taking the release rate at each time point as a dependent variable, and the acetamiprid content ($Ac_{SA}$) and the hydrophilic white carbon content ($Ca_{SA}$) as independent variables.

Equation A: estimated release rate of acetamiprid after 15 minutes $$Y_{evA}(0.25)=0.524 \times Ac_{SA}+1.422 \times Ca_{SA}-6.009$$

Equation B: estimated release rate of acetamiprid after 4 hours $$Y_{evA}(4)=0.745 \times Ac_{SA}+2.135 \times Ca_{SA}-7.234$$

Equation C: estimated release rate of acetamiprid after 24 hours $$Y_{evA}(24)=1.014 \times Ac_{SA}+2.599 \times Ca_{SA}-7.509$$

Equation D: estimated release rate of acetamiprid after 72 hours $$Y_{evA}(72)=1.313 \times Ac_{SA}+2.838 \times Ca_{SA}-6.968$$

Equation E: estimated release rate of acetamiprid after 120 hours $$Y_{evA}(120)=1.545 \times Ac_{SA}+2.945 \times Ca_{SA}-7.562$$

Example 1

The acetamiprid content $Ac_{SA}$=5% by mass and the hydrophilic white carbon content $Ca_{SA}$=1% by mass were selected so as to satisfy the equation of: estimated release rate $Y_{evA}$(0.25)=−1.97% by mass, which had been calculated from the Equation A mentioned above. The agricultural chemical-containing resin composition (wettable powder 1) with the selected composition ratio was prepared by the following manner.

2.5 g of pure acetamiprid, 47.0 g of SMA17352P (a styrene-maleic anhydride copolymer having a molecular weight of 7000, manufactured by Sartomer Company Inc.), and 0.5 g of Carplex #80D (hydrophilic white carbon having a hydrophobicity of 0%, manufactured by Shionogi & Co., Ltd.) were weighed and put in a 1000 ml eggplant flask. About 200 ml of acetone was charged therein. The mixture was dissolved and dispersed in an ultrasonic bath. The major part of the solvent was removed from this solution by distillation using an evaporator. The residue was taken out from the flask. This residue was pulverized in a mortar, and dried by a vacuum dryer at 40° C. for 2.5 hours, thereby yielding a solid matter.

44.1 g of this solid matter was added with 0.45 g of Newkalgen RX-B (sodium lignin sulfonate manufactured by Takemoto Oil & Fat Co., Ltd.) and 0.45 g of Newkalgen BX-C (sodium alkylnaphthalenesulfonate manufactured by Takemoto Oil & Fat Co., Ltd.), and well mixed in a plastic bag. The total amount of this mixture was pulverized using a pin mill, thereby yielding a wettable powder 1 comprising a fine particle composition with an average particle diameter of 17.9 μm. The estimated release rate $Y_{evA}$(0.25) obtained by the Equation A included an error of about 4% relative to the measured release rate; however, it sufficiently achieved the function to design the agricultural chemical-containing resin composition.

Example 2

The acetamiprid content $Ac_{SA}$=5% by mass and the hydrophilic white carbon content $Ca_{SA}$=5% by mass were selected so as to satisfy the equation of: estimated release rate $Y_{evA}$(0.25)=3.72% by mass, which had been calculated from the Equation A mentioned above. The agricultural chemical-containing resin composition with the selected composition ratio was prepared by the same procedure as that of Example 1, thereby yielding a wettable powder 2 comprising a fine particle composition with an average particle diameter of 15.2 μM.

Example 3

The acetamiprid content $Ac_{SA}$=5% by mass and the hydrophilic white carbon content $Ca_{SA}$=10% by mass were selected so as to satisfy the equation of: estimated release rate $Y_{evA}$(0.25)=10.8% by mass, which had been calculated from the Equation A mentioned above. The agricultural chemical-containing resin composition with the selected composition ratio was prepared by the same procedure as that of Example 1, thereby yielding a wettable powder 3 comprising a fine particle composition with an average particle diameter of 14.0 μm.

Example 4

The acetamiprid content $Ac_{SA}$=30% by mass and the hydrophilic white carbon content $Ca_{SA}$=1% by mass were selected so as to satisfy the equation of: estimated release rate $Y_{evA}$(0.25)=11.1% by mass, which had been calculated from the Equation A mentioned above. The agricultural chemical-containing resin composition with the selected composition ratio was prepared by the same procedure as that of Example 1, thereby yielding a wettable powder 4 comprising a fine particle composition with an average particle diameter of 12.7 μm.

Example 5

The acetamiprid content $Ac_{SA}$=30% by mass and the hydrophilic white carbon content $Ca_{SA}$=5% by mass were selected so as to satisfy the equation of: estimated release rate $Y_{evA}$(0.25)=16.8% by mass, which had been calculated from the Equation A mentioned above. The agricultural chemical-containing resin composition with the selected composition ratio was prepared by the same procedure as that of Example 1, thereby yielding a wettable powder 5 comprising a fine particle composition with an average particle diameter of 14.2 μm.

Example 6

The acetamiprid content $Ac_{SA}$=30% by mass and the hydrophilic white carbon content $Ca_{SA}$=10% by mass were selected so as to satisfy the equation of: estimated release rate $Y_{evA}$(0.25)=23.9% by mass, which had been calculated from the Equation A mentioned above. The agricultural chemical-containing resin composition with the selected composition ratio was prepared by the same procedure as that of Example 1, thereby yielding a wettable powder 6 comprising a fine particle composition with an average particle diameter of 16.6 μm.

Example 7

The acetamiprid content $Ac_{SA}$=35% by mass and the hydrophilic white carbon content $Ca_{SA}$=1% by mass were selected so as to satisfy the equation of: estimated release rate $Y_{evA}$(0.25)=13.8% by mass, which had been calculated from the Equation A mentioned above. The agricultural chemical-containing resin composition with the selected composition ratio was prepared by the same procedure as that of Example 1, thereby yielding a wettable powder 7 comprising a fine particle composition with an average particle diameter of 14.9 μm.

Example 8

The acetamiprid content $Ac_{SA}$=35% by mass and the hydrophilic white carbon content $Ca_{SA}$=5% by mass were selected so as to satisfy the equation of: estimated release rate $Y_{evA}$(0.25)=19.4% by mass, which had been calculated from the Equation A mentioned above. The agricultural chemical-containing resin composition with the selected composition ratio was prepared by the same procedure as that of Example 1, thereby yielding a wettable powder 8 comprising a fine particle composition with an average particle diameter of 17.2 μm.

Example 9

The acetamiprid content $Ac_{SA}$=35% by mass and the hydrophilic white carbon content $Ca_{SA}$=10% by mass were selected so as to satisfy the equation of: estimated release rate $Y_{evA}$(0.25)=26.6% by mass, which had been calculated from The respective equations were statistically significant, and the coefficients of $Ac_{SA}$ and $Ca_{SA}$ respectively showed 99% or higher significance.

the Equation A mentioned above. The agricultural chemical-containing resin composition with the selected composition ratio was prepared by the same procedure as that of Example 1, thereby yielding a wettable powder 9 comprising a fine particle composition with an average particle diameter of 23.2 μm.

Water Releasability Test

The wettable powders 1 to 9 were respectively weighed precisely so that each sample can contain 10 mg of pure acetamiprid, and put in a 100 ml vial container. Then, 80 ml of 25° C. distilled water and 20 ml of a methyl 4-hydroxybenzoate solution (500 mg/liter of distilled water) as an internal standard were added therein. The container was sealed, inverted five times, and left still in a thermostatic chamber at 25° C. until the time of sampling. After a predetermined period of time, the container was inverted five times. Next, about 0.7 ml of the solution was sampled out (filtrated with a 0.45 μm filter). The concentration of acetamiprid in the sampled solution was measured by HPLC. The measured release rate was calculated by percentage with respect to the concentration of acetamiprid assuming that acetamiprid in the wettable powder had been all dissolved with water. The results are shown in Table 2.

TABLE 2

|  | $Ac_A$ (% by mass) | $Ca_A$ (% by mass) | Average particle diameter (μm) | Measured release rate of acetamiprid (% by mass) after elapsed time | | | | |
|---|---|---|---|---|---|---|---|---|
|  |  |  |  | 15 minutes | 4 hours | 24 hours | 72 hours | 120 hours |
| Example 1 | 5.0 | 1.0 | 17.9 | 1.9 | 3.6 | 5.9 | 8.2 | 9.1 |
| Example 2 | 5.0 | 5.0 | 15.2 | 3.5 | 6.8 | 10.1 | 13.3 | 14.2 |
| Example 3 | 5.0 | 10.0 | 14.0 | 6.9 | 12.8 | 18.0 | 22.6 | 23.8 |
| Example 4 | 30.0 | 1.0 | 12.7 | 10.8 | 17.2 | 24.7 | 33.2 | 40.0 |
| Example 5 | 30.0 | 5.0 | 14.2 | 16.2 | 24.8 | 33.7 | 43.6 | 51.0 |
| Example 6 | 30.0 | 10.0 | 16.6 | 26.6 | 40.6 | 53.5 | 66.6 | 75.7 |
| Example 7 | 35.0 | 1.0 | 14.9 | 11.3 | 18.1 | 27.9 | 40.6 | 49.1 |
| Example 8 | 35.0 | 5.0 | 17.2 | 18.4 | 27.3 | 39.5 | 52.1 | 57.5 |
| Example 9 | 35.0 | 10.0 | 23.2 | 28.7 | 42.7 | 56.7 | 69.1 | 77.4 |

Example 10

The acetamiprid content $Ac_{SA}$=30.0% by mass and the hydrophilic white carbon content $Ca_{SA}$=1.0% by mass were selected so as to satisfy the equation of: estimated release rate $Y_{evA}(0.25)$=11.1% by mass, which had been calculated from the Equation A mentioned above. The agricultural chemical-containing resin composition with the selected composition ratio was prepared by the same procedure as that of Example 1, thereby yielding a wettable powder 10 comprising a fine particle composition with an average particle diameter of 7.9 μm.

Example 11

The acetamiprid content $Ac_{SA}$=30.0% by mass and the hydrophilic white carbon content $Ca_{SA}$=0.5% by mass were selected so as to satisfy the equation of: estimated release rate $Y_{evA}(0.25)$=10.4% by mass, which had been calculated from the Equation A mentioned above. The agricultural chemical-containing resin composition with the selected composition ratio was prepared by the same procedure as that of Example 1, thereby yielding a wettable powder 11 comprising a fine particle composition with an average particle diameter of 13.3 μm.

Example 12

The acetamiprid content $Ac_{SA}$=30.0% by mass and the hydrophilic white carbon content $Ca_{SA}$=0.1% by mass were selected so as to satisfy the equation of: estimated release rate $Y_{evA}(0.25)$=9.85% by mass, which had been calculated from the Equation A mentioned above. The agricultural chemical-containing resin composition with the selected composition ratio was prepared by the same procedure as that of Example 1, thereby yielding a wettable powder 12 comprising a fine particle composition with an average particle diameter of 12.6 μm.

Comparative Example 1

The acetamiprid content $Ac_{SA}$=93.5% by mass and the hydrophilic white carbon content $Ca_{SA}$=6.5% by mass were selected so as to satisfy the equation of: estimated release rate $Y_{evA}(0.25)$=52.2% by mass, which had been calculated from the Equation A mentioned above. The agricultural chemical-containing resin composition (wettable powder A) with the selected composition ratio was prepared by the following manner.

72.3 g of acetamiprid, 2.5 g of Newkalgen RX-B, 20.2 g of clay, and 5.0 g of Carplex #80D were well mixed in a mortar, and then pulverized by an air pulverizer, thereby yielding a wettable powder A.

Comparative Example 2

The acetamiprid content $Ac_{SA}$=5% by mass and the hydrophilic white carbon content $Ca_{SA}$=50% by mass were selected so as to satisfy the equation of: estimated release rate $Y_{evA}(0.25)$=67.7% by mass, which had been calculated from the Equation A mentioned above. The bulk powder B comprising the agricultural chemical-containing resin composition with the selected composition ratio was prepared by the following manner.

1 g of acetamiprid, 9 g and SMA3000 (a styrene-maleic anhydride copolymer based resin having a molecular weight of 9500, manufactured by Sartomer Company Inc.), and 10 g of Carplex #80D (hydrophilic white carbon manufactured by Shionogi & Co., Ltd.) were weighed and put in a 300 ml eggplant flask. 100 ml of dichloromethane was charged therein and all dissolved in an ultrasonic bath. The major part of the solvent was removed from this solution by distillation using an evaporator. Furthermore, the remaining matter was dried by a vacuum dryer at 40° C. for 2 hours, thereby yielding a solid matter. This solid matter was well ground in a mortar and pulverized. Particles from 44 μm to 105 μm were selected by sifting through sieves having sieve opening sizes of 44 μm and 105 μm, thereby yielding a fine particle composition (bulk powder B) with an average particle diameter of 82 μm.

The compositions obtained by Examples 10 to 12 and Comparative Examples 1 and 2 were subjected to the same water releasability test as that of above-mentioned test. In Examples 10 to 12, the test was carried out for 360 hours. In Comparative Examples 1 and 2, the test had to be stopped in the middle because the measured release rate was saturated. These results are shown in Table 3.

using an evaporator. The residue was taken out from the flask. The residue was pulverized in a mortar, and dried by a vacuum dryer at 40° C. for 2.5 hours. Then, the resultant product was separated by sifting through a sieve having a sieve opening size of 44 μm, thereby yielding a solid matter with a particle diameter of 44 μm or smaller.

4.41 g of the solid matter was added with 0.045 g of Newkalgen RX-B (sodium lignin sulfonate manufactured by Takemoto Oil & Fat Co., Ltd.) and 0.045 g of Newkalgen BX-C (sodium alkylnaphthalenesulfonate manufactured by

TABLE 3

| | $Ac_A$ | $Ca_A$ | Average particle | Measured release rate of acetamiprid (% by mass) after elapsed time | | | | | | |
|---|---|---|---|---|---|---|---|---|---|---|
| | (% by mass) | (% by mass) | diameter (μm) | 15 minutes | 4 hours | 24 hours | 72 hours | 120 hours | 264 hours | 360 hours |
| Example 10 | 30.0 | 1.0 | 7.9 | 10.1 | 17.5 | 25.3 | 37.8 | 45.5 | 65.3 | 75.1 |
| Example 11 | 30.0 | 0.5 | 13.3 | 7.6 | 13.4 | 20.1 | 29.7 | 36.2 | 53.1 | 59.9 |
| Example 12 | 30.0 | 0.1 | 12.6 | 6.6 | 11.4 | 19.3 | 28.1 | 34.1 | 50.4 | 55.4 |
| Comparative Example 1 | 93.5 | 6.5 | — | 100.0 | 100.0 | Not measured | Not measured | Not measured | Not measured | Not measured |
| Comparative Example 2 | 5.0 | 50.0 | 82.0 | 60.1 | 60.3 | 66.1 | 67.6 | Not measured | Not measured | Not measured |

As shown in Table 3, with the wettable powder A whose estimated release rate $Y_{evA}(0.25)$ exceeded 40% by mass, the measured release rate reached 100% after 15 minutes. Thus, it is anticipated that the agricultural chemical would rapidly act on field crops and such phytotoxicity would occur, and residual effect would not be given. Moreover, with the bulk powder B whose estimated release rate $Y_{evA}(0.25)$ exceeded 40% by mass, the measured release rate reached 60% after 15 minutes (that is to say, the initial burst phenomenon did occur), and thereafter the measured release rate was undergone very little change.

On the other hand, as shown in Table 2 and Table 3, with the wettable powders 1 to 12 satisfying the in equation of: estimated release rate $Y_{evA}(0.25)$ 40% by mass, produced by the method of the present invention, the abundant release soon after charging in water (initial burst) was suppressed and thereafter the measured release rate was appropriately controlled. The equations to estimate the release rate $Y_{evA}$ employed in the Examples had been determined on the basis of data up to 120 hours. However, even after 360 hours, the measured release rate showed an appropriate profile, and no dead stock was brought about (refer to Examples 10 to 12).

Example 13

The imidacloprid content $Ac_{SA}=5\%$ by mass and the hydrophilic white carbon content $Ca_{SA}=1\%$ by mass were selected so as to satisfy the equation of: estimated release rate $Y_{evA}(0.25)=-1.97\%$ by mass, which had been calculated from the Equation A mentioned above. The agricultural chemical-containing resin composition (wettable powder 13) with the selected composition ratio was prepared by the following manner.

0.5 g of pure imidacloprid, 9.4 g of SMA17352P (a styrene-maleic anhydride copolymer having a molecular weight of 7000, manufactured by Sartomer Company Inc.), and 0.1 g of Carplex #80D (hydrophilic white carbon having a hydrophobicity of 0%, manufactured by Shionogi & Co., Ltd.) were weighed and put in a 300 ml eggplant flask. Then, about 50 ml of dichloromethane was added thereto. The mixture was dissolved and dispersed in an ultrasonic bath. The major part of the solvent was removed from this solution by distillation Takemoto Oil & Fat Co., Ltd.), and well mixed in a plastic bag, thereby yielding a wettable powder 13 comprising a fine particle composition with an average particle diameter of 19.9 μm. The estimated release rate $Y_{evA}(0.25)$ obtained by the Equation A included an error of about 4% relative to the measured release rate; however, it sufficiently achieved the function to design the agricultural chemical-containing resin composition.

Example 14

The imidacloprid content $Ac_{SA}=5\%$ by mass and the hydrophilic white carbon content $Ca_{SA}=5\%$ by mass were selected so as to satisfy the equation of: estimated release rate $Y_{evA}(0.25)=3.72\%$ by mass, which had been calculated from the Equation A mentioned above. The agricultural chemical-containing resin composition with the selected composition ratio was prepared by the same procedure as that of Example 13, thereby yielding a wettable powder 14 comprising a fine particle composition with an average particle diameter of 22.0 μm.

Example 15

The imidacloprid content $Ac_{SA}=5\%$ by mass and the hydrophilic white carbon content $Ca_{SA}=10\%$ by mass were selected so as to satisfy the equation of: estimated release rate $Y_{evA}(0.25)=10.8\%$ by mass, which had been calculated from the Equation A mentioned above. The agricultural chemical-containing resin composition with the selected composition ratio was prepared by the same procedure as that of Example 13, thereby yielding a wettable powder 15 comprising a fine particle composition with an average particle diameter of 24.5 μm.

Example 16

The imidacloprid content $Ac_{SA}=30\%$ by mass and the hydrophilic white carbon content $Ca_{SA}=1\%$ by mass were selected so as to satisfy the equation of: estimated release rate $Y_{evA}(0.25)=11.1\%$ by mass, which had been calculated from the Equation A mentioned above. The agricultural chemical-containing resin composition with the selected composition ratio was prepared by the same procedure as that of Example 13, thereby yielding a wettable powder 16 comprising a fine particle composition with an average particle diameter of 19.2 μm.

Example 17

The imidacloprid content $Ac_{SA}$=30% by mass and the hydrophilic white carbon content $Ca_{SA}$=5% by mass were selected so as to satisfy the equation of: estimated release rate $Y_{evA}$(0.25)=16.8% by mass, which had been calculated from the Equation A mentioned above. The agricultural chemical-containing resin composition with the selected composition ratio was prepared by the same procedure as that of Example 13, thereby yielding a wettable powder 17 comprising a fine particle composition with an average particle diameter of 21.1 μm.

Example 18

The imidacloprid content $Ac_{SA}$=35% by mass and the hydrophilic white carbon content $Ca_{SA}$=1% by mass were selected so as to satisfy the equation of: estimated release rate $Y_{evA}$(0.25)=13.8% by mass, which had been calculated from the Equation A mentioned above. The agricultural chemical-containing resin composition with the selected composition ratio was prepared by the same procedure as that of Example 13, thereby yielding a wettable powder 18 comprising a fine particle composition with an average particle diameter of 19.9 μm.

Example 19

The imidacloprid content $Ac_{SA}$=35% by mass and the hydrophilic white carbon content $Ca_{SA}$=5% by mass were selected so as to satisfy the equation of: estimated release rate $Y_{evA}$(0.25)=19.4% by mass, which had been calculated from the Equation A mentioned above. The agricultural chemical-containing resin composition with the selected composition ratio was prepared by the same procedure as that of Example 13, thereby yielding a wettable powder 19 comprising a fine particle composition with an average particle diameter of 22.5 μm.

Water Releasability Test

The wettable powders 13 to 19 were respectively weighed precisely so that each sample can contain 10 mg of pure imidacloprid, and put in a 100 ml vial container. Then, 80 ml of 25° C. distilled water and 20 ml of a methyl 4-hydroxybenzoate solution (500 mg/liter of distilled water) as an internal standard were added therein. The container was sealed, inverted five times, and left still in a thermostatic chamber at 25° C. until the time of sampling. After a predetermined period of time, the container was inverted five times. Next, about 0.7 ml of the solution was sampled out (filtrated with a 0.45 μm filter). The concentration of imidacloprid in the sampled solution was measured by HPLC. The measured release rate was calculated by percentage with respect to the concentration of imidacloprid assuming that imidacloprid in the wettable powder had been all dissolved with water. The results are shown in Table 4.

TABLE 4

| | $Ac_A$ (% by mass) | $Ca_A$ (% by mass) | Particle diameter (D50, μm) | Measured release rate of imidacloprid (% by mass) after elapsed time | | | | | |
|---|---|---|---|---|---|---|---|---|---|
| | | | | 0 h | 0.25 h | 4 h | 24 h | 72 h | 120 h |
| Example 13 | 5 | 1 | 19.9 | 0.0 | 2.0 | 5.5 | 7.9 | 13.0 | 19.3 |
| Example 14 | 5 | 5 | 22.0 | 0.0 | 3.9 | 12.0 | 15.9 | 22.2 | 28.8 |
| Example 15 | 5 | 10 | 24.5 | 0.0 | 9.8 | 18.9 | 23.3 | 32.7 | 40.2 |
| Example 16 | 30 | 1 | 19.2 | 0.0 | 8.4 | 15.5 | 23.3 | 36.9 | 47.9 |
| Example 17 | 30 | 5 | 21.1 | 0.0 | 15.5 | 28.4 | 39.8 | 51.2 | 60.8 |
| Example 18 | 35 | 1 | 19.9 | 0.0 | 14.8 | 23.9 | 29.9 | 44.0 | 58.2 |
| Example 19 | 35 | 5 | 22.5 | 0.0 | 29.4 | 39.9 | 50.2 | 65.4 | 76.3 |

From these results, it is understood that the production method of the present invention is capable of readily designing and producing an agricultural chemical-containing resin composition or an agricultural chemical formulation with which phytotoxicity can be suppressed but sufficient residual effect can be given.

INDUSTRIAL APPLICABILITY

The method for, producing an agricultural chemical-containing resin composition of the present invention is capable of readily designing and producing an agricultural chemical-containing resin composition and an agricultural chemical formulation with which the phenomenon, namely initial burst, in which the agricultural chemical active ingredient is abundantly released within a short period of time, is suppressed to an adequate level, and the phenomenon, namely dead stock, in which the agricultural chemical active ingredient that should be fundamentally released but nonetheless remains by failing to be completely released, is suppressed. In addition, with the agricultural chemical-containing resin composition and the agricultural chemical formulation of the present invention, phytotoxicity due to the increase of the crop residue amount of the agricultural chemical active ingredient would not occur while maintaining the residual effect, and furthermore, remaining in the environment can be avoided. Moreover, in addition to the above-mentioned effects, the agricultural chemical-containing resin composition and the agricultural chemical formulation of the present invention have an effect to improve the residual effect of the agricultural chemical active ingredient, an effect to reduce the wash out into the environment, an effect to reduce the total spay amount, an effect to reduce the number of times of spraying, and an effect to alleviate the toxicity to the sprayer, because of the enhanced light stability, the volatility control, and the enhanced rain resistance, and thus are particularly useful as a seed treating agent and a soil treating agent. The present invention is remarkably useful for the industry from the reasons mentioned above.

The invention claimed is:

1. A solid agricultural chemical-containing resin composition comprising:
    5-35% by mass of an agricultural chemical active ingredient A having a water solubility of 100 ppm or higher at 25° C. selected from the group consisting of nitenpyram, imidacloprid, acetamiprid, thiamethoxam, clothianidin, thiacloprid, dinotefuran and mixtures thereof,
    a styrene-maleic anhydride copolymer or a styrene-maleic anhydride copolymer-mixed resin, and
    at least 0.1% by mass of a hydrophilic white carbon with a hydrophobicity of 20% or lower,
    wherein (1) a sample of said resin composition that contains 10 mg of the agricultural chemical active ingredient A has a release of said active ingredient A not higher than 40% by mass 15 minutes after being added to 80 ml of 25° C. distilled water, and (2) the composition has an average particle diameter of from 10 to 25 μm.

2. The solid agricultural chemical-containing resin composition according to claim 1, wherein the agricultural chemical active ingredient A is acetamiprid.

3. A method for producing an agricultural chemical-containing resin composition according to claim 1 comprising:
    homogeneously mixing 5-35% by mass of an agricultural chemical active ingredient A, a styrene-maleic anhydride copolymer or a styrene-maleic anhydride copolymer-mixed resin, and at least 0.1% by mass of a hydrophilic white carbon to obtain a solid mass in which all of the agricultural chemical active ingredient A, the styrene-maleic anhydride copolymer or the styrene-maleic anhydride copolymer-mixed resin, and the hydrophilic white carbon are homogeneously mixed within the same solid mass, and
    granulating the solid mass to an average particle diameter from 10 to 25 μm,
    wherein (1) a sample of said resin composition that contains 10 mg of the agricultural chemical active ingredient A has a release of said active ingredient A not higher than 40% by mass 15 minutes after being added to 80 ml of 25° C. distilled water, (2) the agricultural chemical active ingredient A is selected from the group consisting of nitenpyram, imidacloprid, acetamiprid, thiamethoxam, clothianidin, thiacloprid, dinotefuran and mixtures thereof, and (3) the hydrophobicity of the hydrophilic white carbon is 20% or lower.

4. The method for producing an agricultural chemical-containing resin composition according to claim 3, wherein the agricultural chemical active ingredient A is acetamiprid.

5. The method for producing an agricultural chemical-containing resin composition according to claim 3, wherein the styrene-maleic anhydride copolymer-mixed resin is a mixture of a styrene-maleic anhydride copolymer with rosin or a derivative thereof, or a polymer derived from salicylic acid or a linear polysalicylate, wherein the rosin derivative is selected from the group consisting of tall rosin, rosin-modified phenol and rosin-modified maleic acid.

6. The method for producing an agricultural chemical-containing resin composition according to claim 3, wherein the granulation is performed by at least one type of method selected from the group consisting of a tumbling granulation process, an agitation granulation process, an extrusion granulation process, a rolling granulation process, a crushing granulation process, and a fluidized granulation process.

7. A bulk powder comprising the agricultural chemical-containing resin composition according to claim 1.

8. An agricultural chemical formulation including the bulk powder according to claim 7.

9. The agricultural chemical formulation according to claim 8, wherein the average particle diameter of the bulk powder is 200 μm or smaller.

* * * * *